(12) United States Patent
Soejima

(10) Patent No.: US 10,585,017 B2
(45) Date of Patent: Mar. 10, 2020

(54) DIAGNOSIS APPARATUS

(71) Applicant: SUBARU CORPORATION, Tokyo (JP)

(72) Inventor: Hideki Soejima, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 0 days.

(21) Appl. No.: 16/227,356

(22) Filed: Dec. 20, 2018

(65) Prior Publication Data

US 2019/0265126 A1 Aug. 29, 2019

(30) Foreign Application Priority Data

Feb. 26, 2018 (JP) .................................. 2018-032200

(51) Int. Cl.
| | | |
|---|---|---|
| G01N 21/00 | (2006.01) | |
| G01M 11/08 | (2006.01) | |
| G01B 11/00 | (2006.01) | |
| G01D 5/353 | (2006.01) | |
| G01N 21/01 | (2006.01) | |
| G01M 11/00 | (2006.01) | |
| G07C 3/00 | (2006.01) | |

(Continued)

(52) U.S. Cl.
CPC ............ *G01M 11/083* (2013.01); *G01B 11/00* (2013.01); *G01D 5/35316* (2013.01); *G01J 1/00* (2013.01); *G01J 3/1895* (2013.01); *G01M 11/00* (2013.01); *G01N 21/01* (2013.01); *G07C 3/00* (2013.01)

(58) Field of Classification Search
CPC . G01M 11/083; G01B 11/00; G01D 5/35316; G01N 21/01

USPC .......................................................... 356/73
See application file for complete search history.

(56) References Cited

U.S. PATENT DOCUMENTS

| 4,592,003 A | 5/1986 | Kobayashi et al. |
| 5,355,208 A | 10/1994 | Crawford et al. |

(Continued)

FOREIGN PATENT DOCUMENTS

| JP | 59-30030 A | 2/1984 |
| JP | 3-94131 A | 4/1991 |

(Continued)

OTHER PUBLICATIONS

Extended European Search Report issued in corresponding EP Application No. 18 20 4357 dated May 20, 2019.

(Continued)

*Primary Examiner* — Sunghee Y Gray
(74) *Attorney, Agent, or Firm* — Troutman Sanders LLP

(57) ABSTRACT

A diagnosis apparatus includes a fiber optic sensor, a collection processor, and a self-diagnosis processor. The fiber optic sensor is configured to be disposed over a target. The collection processor is configured to perform a collection process that collects measurement data related to the target obtained by the fiber optic sensor. The self-diagnosis processor is configured to perform a self-diagnosis process before the collection processor starts the collection process. The self-diagnosis process obtains an output value related to calibration of the fiber optic sensor, causes the collection processor to start the collection process when the output value falls within a proper range, and outputs an error when the output value falls outside the proper range.

5 Claims, 3 Drawing Sheets

(51) Int. Cl.
*G01J 1/00* (2006.01)
*G01J 3/18* (2006.01)

(56) References Cited

U.S. PATENT DOCUMENTS

| | | | |
|---|---|---|---|
| 6,606,490 B1* | 8/2003 | Rainish | H04W 52/0235 |
| | | | 455/343.1 |
| 10,221,825 B2* | 3/2019 | Ota | F02P 9/002 |
| 2005/0067559 A1* | 3/2005 | Ogisu | G01M 11/086 |
| | | | 250/227.14 |
| 2008/0158552 A1* | 7/2008 | Tokunaga | G01N 21/253 |
| | | | 356/73 |
| 2008/0234890 A1* | 9/2008 | Okada | G01P 1/127 |
| | | | 701/33.4 |
| 2011/0037841 A1* | 2/2011 | Shibasaki | A61B 1/0008 |
| | | | 348/68 |
| 2014/0218751 A1 | 8/2014 | Soejima et al. | |
| 2015/0112640 A1* | 4/2015 | Niro | G01D 15/00 |
| | | | 702/183 |
| 2016/0135755 A1* | 5/2016 | Lu | A61B 5/0022 |
| | | | 600/301 |
| 2017/0082766 A1 | 3/2017 | Milne et al. | |
| 2017/0370786 A1 | 12/2017 | Mastrianni et al. | |
| 2018/0026720 A1 | 1/2018 | Yi et al. | |

FOREIGN PATENT DOCUMENTS

| | | |
|---|---|---|
| JP | 5-172653 A | 7/1993 |
| JP | 11-51784 A | 2/1999 |
| JP | 2003-344147 A | 12/2003 |
| JP | 2005-98921 A | 4/2005 |
| JP | 2007-178258 A | 7/2007 |
| JP | 2015-75446 A | 4/2015 |
| JP | 6159095 B2 | 7/2017 |
| JP | 2018-504603A T | 2/2018 |

OTHER PUBLICATIONS

Notice of Reasons for Refusal issued in corresponding Japanese Patent Application No. 2015-032200 dated Oct. 8, 2019 (with machine translation).

* cited by examiner

DIAGNOSIS APPARATUS

CROSS-REFERENCE TO RELATED APPLICATIONS

The present application claims priority from Japanese Patent Application No. 2018-032200 filed on Feb. 26, 2018, the entire contents of which are hereby incorporated by reference.

BACKGROUND

The technology relates to a diagnosis apparatus.

A fiber optic sensor allows for measurement of a physical quantity, a chemical quantity, or any other quantity of a target. For example, light is emitted from a light source and travels through an optical fiber to reach a measurement point at which the target is disposed. A characteristic of the light, such as an intensity, a phase, a frequency, a wavelength, or a polarization, can change due to a disturbance attributable to the target. The fiber optic sensor measures the quantity of the target through measuring such a characteristic of the light by means of a light receiver. For example, reference is made to Japanese Unexamined Patent Application Publication No. 2005-98921 and Japanese Patent No. 6159095.

SUMMARY

An aspect of the technology provides a diagnosis apparatus that includes: a fiber optic sensor configured to be disposed over a target; a collection processor configured to perform a collection process that collects measurement data related to the target obtained by the fiber optic sensor; and a self-diagnosis processor configured to perform a self-diagnosis process before the collection processor starts the collection process. The self-diagnosis process obtains an output value related to calibration of the fiber optic sensor, causes the collection processor to start the collection process when the output value falls within a proper range, and outputs an error when the output value falls outside the proper range.

An aspect of the technology provides a diagnosis apparatus that includes: a fiber optic sensor configured to be disposed over a target; and circuitry configured to obtain, before collecting measurement data related to the target obtained by the fiber optic sensor, an output value related to calibration of the fiber optic sensor, start collecting the measurement data related to the target when the output value falls within a proper range, and output an error when the output value falls outside the proper range.

BRIEF DESCRIPTION OF THE DRAWINGS

FIG. 2A and FIG. 2B are diagrams that describe a vibrator and a fiber optic sensor illustrated in FIG. 1, in which FIG. 2A illustrates an example in which the vibrator and the fiber optic sensor are provided over a target, and FIG. 2B illustrates an example of an internal structure of the fiber optic sensor.

DETAILED DESCRIPTION

Figure 1:
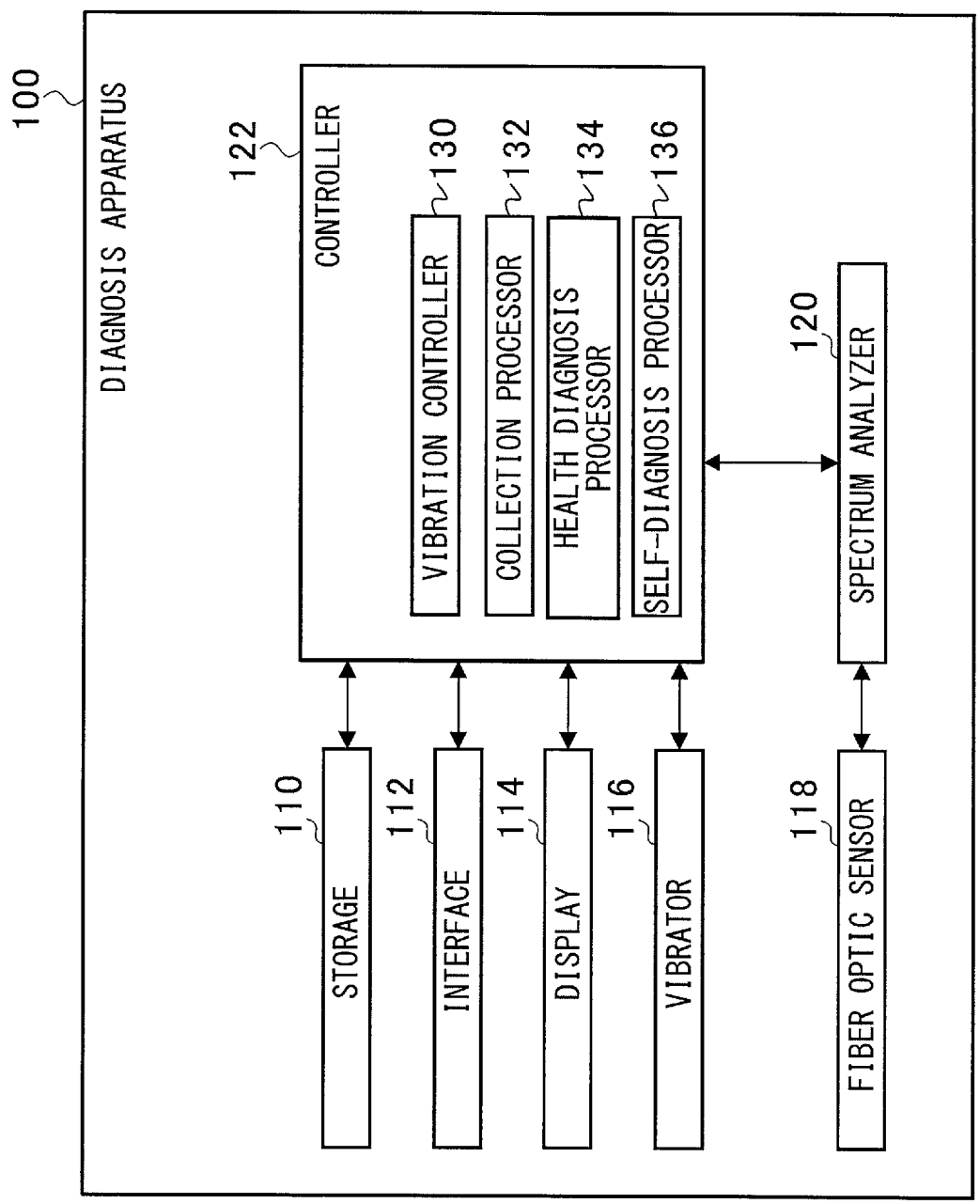
FIG. 1 is a block diagram illustrating an example of a configuration of a diagnosis apparatus according to one implementation of the technology.

In the following, some implementations of the technology are described in detail with reference to the accompanying drawings. Note that sizes, materials, specific values, and any other factors illustrated in respective implementations are illustrative for easier understanding of the technology, and are not intended to limit the scope of the technology unless otherwise specifically stated. Further, elements in the following example implementations which are not recited in a most-generic independent claim of the disclosure are optional and may be provided on an as-needed basis. The drawings are schematic and are not intended to be drawn to scale. Throughout the present specification and the drawings, elements having substantially the same function and configuration are denoted with the same reference numerals to avoid any redundant description. Further, elements that are not directly related to the technology are unillustrated in the drawings.

A fiber optic sensor is higher in durability than an electrical sensor and allows for automatic measurement for a long period of time. However, full automation of the measurement that utilizes the fiber optic sensor is difficult if human resources are required to check whether the fiber optic sensor itself functions normally.

It is desirable to provide a diagnosis apparatus that makes it possible to automate measurement that utilizes a fiber optic sensor.

FIG. 1 is a block diagram illustrating an example of a configuration of a diagnosis apparatus 100 according to an example implementation of the technology. Referring to FIG. 1, the diagnosis apparatus 100 may include a storage 110, an interface 112, a display 114, a vibrator 116, a fiber optic sensor 118, a spectrum analyzer 120, and a controller 122.

The storage 110 may include a random-access memory (RAM), a flash memory, a hard disk drive (HDD), or any other data storage medium. The storage 110 may contain table information related to a later-described proper range for calibration. The interface 112 may include one or more of devices such as a keyboard or a touch panel that is overlaid on the display 114. The interface 112 may accept an input operation performed by a user. The display 114 may include a liquid crystal display, an organic electroluminescence (EL) display, or a display of any other type.

The vibrator 116 may have a plurality of piezoelectric elements. For example, the piezoelectric elements may be attached to a sheet.

Figure 2A:
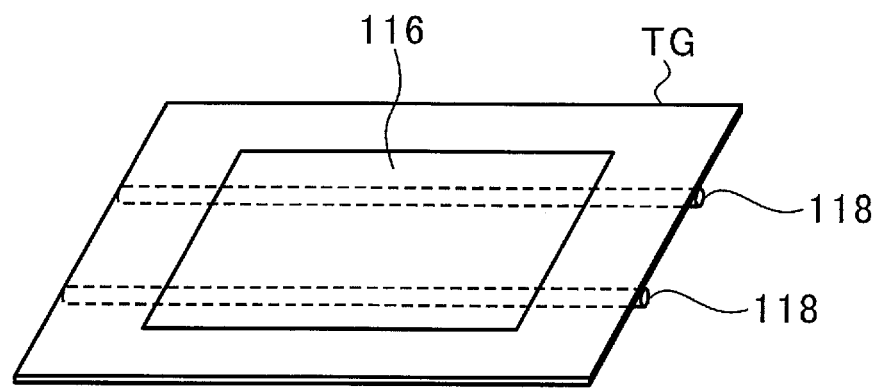
Figure 2B:
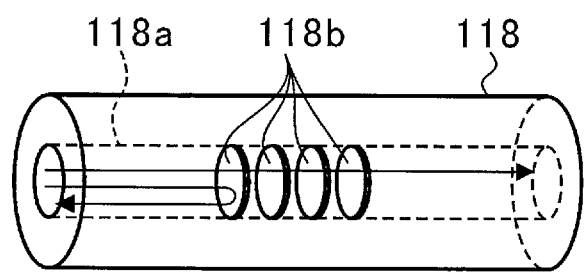

FIG. 2A and FIG. 2B are diagrams that describe the vibrator 116 and the fiber optic sensor 118. FIG. 2A illustrates an example in which the vibrator 116 and the fiber optic sensor 118 are provided over a target TG. FIG. 2B illustrates an example of an internal structure of the fiber optic sensor 118.

The target TG may be a part of a structure. Non-limiting examples of the structure may include an aircraft and a building. In an example implementation, the target TG may include a plurality of targets TG. For example, the vibrator 116 and the fiber optic sensor 118 may be provided for each of the targets TG. In the following, a description is given of an example implementation where the target TG is a plate-shaped member, although the target TG can have any shape. The vibrator 116 and the fiber optic sensor 118 may be attached to or placed over the target TG in a suitable way, in accordance with the shape of the target TG.

The piezoelectric element of the vibrator 116 may be coupled to an unillustrated electric conductor, allowing a thickness of the piezoelectric element to vary by a piezoelectric effect upon application of a voltage to the piezoelectric element from the electric conductor. Applying a pulsed voltage to any of the piezoelectric elements may cause a vibration at a part of the target TG which is near the piezoelectric element applied with the voltage. In this example way, the vibrator 116 may vibrate the target TG.

The fiber optic sensor 118 may be an intrinsic fiber optic sensor. In such an example implementation, an optical fiber of the fiber optic sensor 118 itself may function as a sensor device. In an alternative example implementation, the fiber optic sensor 118 may be an extrinsic fiber optic sensor in which the optical fiber serves only as a transmission line that transmits light to/from any other sensor device. For example, the fiber optic sensor 118 may be adhered to the target TG by an adhesive.

Referring to FIG. 2B, the fiber optic sensor 118 may have a core 118a positioned inside a coating or a cladding and through which the light passes. The light that travels from the core 118a toward the outer side may be reflected by the cladding and may be thus returned to the core 118a.

The core 118a may include a grating 118b. The grating 118b may have a refractive index different from a refractive index of any other part of the core 118a. The grating 118b may include a plurality of gratings 118b that are so provided as to be separated away from each other in a direction of axis of the optical fiber. Such gratings 118b may cause a refractive index of the optical fiber to change periodically, i.e., may form a Fiber Bragg Grating (FBG).

The gratings 118b may cause components in light that has a broadband spectrum to interfere with each other at a specific wavelength referred to as a Bragg wavelength, such that those components are intensified with respect to each other. The gratings 118b may thus allow a component of the specific wavelength, out of the light having the broadband spectrum, to be reflected from the gratings 118b and allow light of any other wavelength to transmit through the gratings 118b.

A wavelength of the light reflected from the gratings 118b may be varied when any disturbance is applied to the gratings 118b. The disturbance applied to the gratings 118b may be measured by measuring the change in the wavelength of the light reflected from the gratings 118b.

Referring to FIG. 1, the spectrum analyzer 120 may be coupled to the fiber optic sensor 118. The spectrum analyzer 120 may have a light source and a light receiver. The light source may emit the light having the broadband spectrum. The light having the broadband spectrum, after being emitted from the light source, may reach the fiber optic sensor 118 at which a part of the light may be reflected as described above. The light receiver of the spectrum analyzer 120 may receive such reflection light.

The spectrum analyzer 120 may detect a light intensity distribution in a predetermined wavelength band. The spectrum analyzer 120 may detect the wavelength of the reflection light received by the light receiver. A signal of the wavelength of the reflection light detected by the spectrum analyzer 120 may be subjected to an analog-to-digital (A/D) conversion by an unillustrated A/D converter. The thus-converted signal of the wavelength of the reflection light may be outputted to the controller 122.

The controller 122 may manage and control the diagnosis apparatus 100 as a whole. The controller 122 may include a semiconductor integrated circuit that have devices including a central processing unit (CPU), a read-only memory (ROM) in which pieces of information including a program are stored, and a random-access memory (RAM) that serves as a work area. The controller 122 may serve as a vibration controller 130, a collection processor 132, a health diagnosis processor 134, and a self-diagnosis processor 136. In one implementation, the controller 122 may serve as one or more of a "vibration controller", a "collection processor", a "health diagnosis processor", and a "self-diagnosis processor".

The vibration controller 130 may apply the voltage to the vibrator 116 to thereby cause the vibrator 116 to apply a vibration to or vibrate the target TG.

The collection processor 132 may perform, on each of the targets TG measurement that utilizes the fiber optic sensors 118. The collection processor 132 may cause the spectrum analyzer 120 to emit the light having the broadband spectrum and to detect the wavelength of the reflection light as described above. The collection processor 132 may measure, with the wavelength of the reflection light, a change in the target TG which has triggered the disturbance applied to the gratings 118b.

A quantity to be measured, such as a physical quantity, may be set in advance for the fiber optic sensor 118. Non-limiting examples of the quantity may include a distortion (e.g., a stress) and a temperature of the target TG. In other words, the diagnosis apparatus 100 may include the fiber optic sensor 118 directed to measurement of the distortion, the fiber optic sensor 118 directed to measurement of the temperature, and/or the fiber optic sensor 118 directed to measurement of any other quantity.

For example, the collection processor 132 may measure the distortion of the target TG, on the basis of the reflection light obtained by the fiber optic sensor 118 directed to the distortion measurement. The collection processor 132 may measure the temperature of the target TG, on the basis of the reflection light obtained by the fiber optic sensor 118 directed to the temperature measurement.

The collection processor 132 may measure the distortion of the target TG on the basis of the reflection light obtained by the fiber optic sensor 118 directed to the distortion measurement, when the target TG is vibrated by the vibrator 116 controlled by the vibration controller 130. This helps to detect a damage of the target TG, owing to a difference in distortion (i.e., vibration) to be measured by the collection processor 132 between a case where the target TG has the damage or any impairment in a region from the piezoelectric element of the vibrator 116 to the fiber optic sensor 118 and a case where the target TG has no such damage or impairment.

The collection processor 132 thus performs a collection process that collects data on the measurement of the target TG obtained by the fiber optic sensor 118.

The health diagnosis processor 134 may perform a health diagnosis process that diagnoses a health of the structure provided with the fiber optic sensor 118, on the basis of the measurement data collected by the collection processor 132. For example, the fiber optic sensor 118 may be attached to the target TG as a part of the aircraft in an example implementation where the diagnosis apparatus 100 is applied to the aircraft as one example of the structure. The collection process, the health diagnosis process, or both may be performed at any timing on or before, or even after, the operation of the aircraft.

The health diagnosis process may diagnose the health of the structure, on the basis of the measurement data on the target TG collected by the collection processor 132. For example, the health diagnosis process may determine that the health is low and output an evaluation value indicating the low health when the damage of the target TG is detected as described above, or when a value of the distortion or the temperature indicates abnormality.

The health diagnosis processor 134 may cause the display 114 to display a result of the health diagnosis process. This allows an operator to perform maintenance, such as checking component parts or replacing the component parts, depending on the result of the health diagnosis process.

It is to be noted that the fiber optic sensor 118 is higher in durability than an electrical sensor and allows for automatic measurement for a long period of time. However, the fiber optic sensor 118 may possibly experience breakage or damage. Further, in an example implementation where the fiber optic sensor 118 is attached to the target TG by the adhesive, the adhesive may possibly come off due to aging degradation. Under such circumstances, full automation of the measurement that utilizes the fiber optic sensor 118 may possibly involve difficulties if human resources are required to check whether the fiber optic sensor 118 itself functions normally.

To automate the measurement that utilizes the fiber optic sensor 118, the self-diagnosis processor 136 performs a self-diagnosis process before the collection processor 132 starts the collection process. In the following, a description is given in detail of the self-diagnosis process by referring to an example flowchart.

Figure 3:
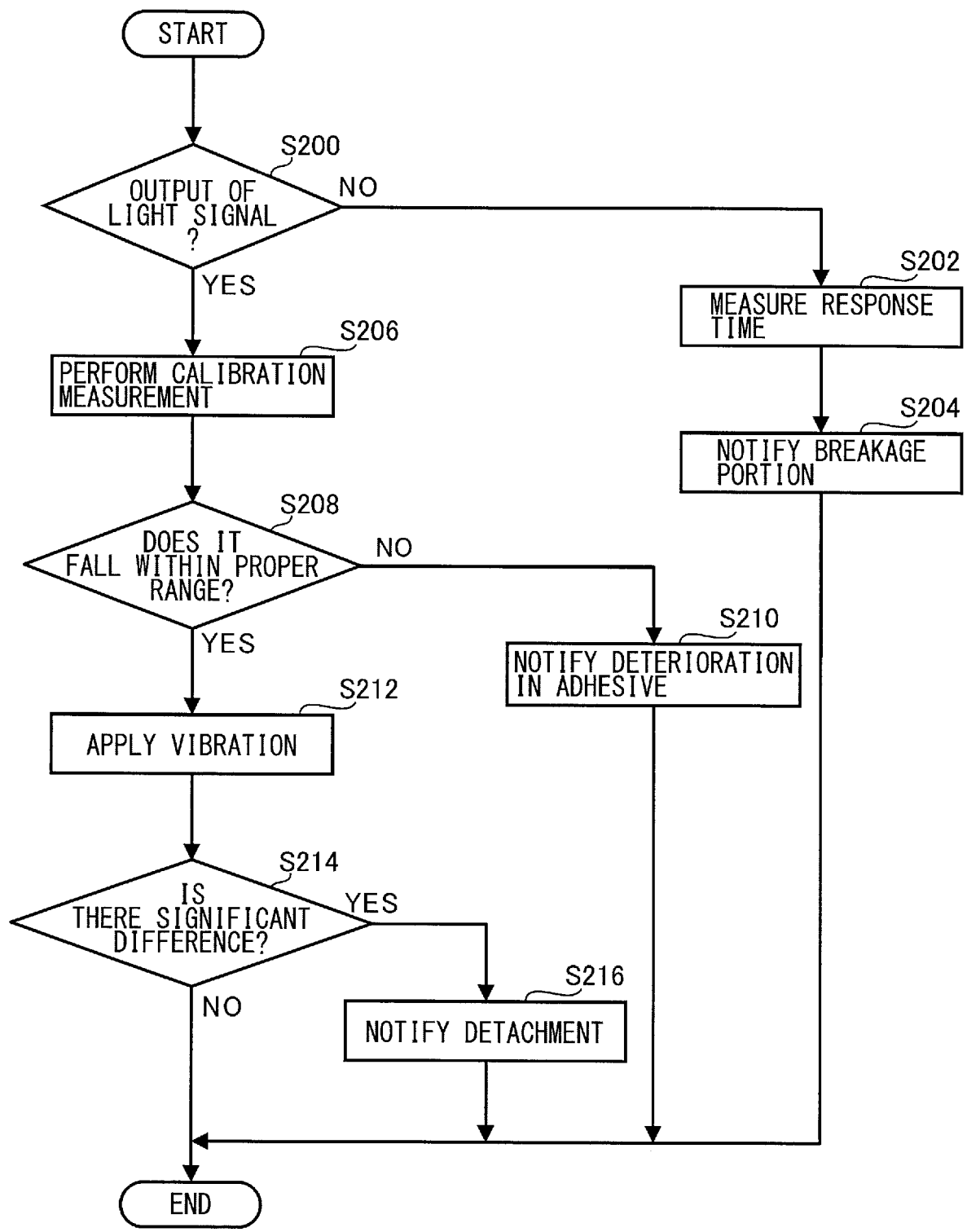
FIG. 3 is a flowchart illustrating an example of a flow of a self-diagnosis process according to one implementation of the technology.

FIG. 3 is a flowchart illustrating an example of a flow of the self-diagnosis process according to an example implementation of the technology. The process illustrated by way of example in FIG. 3 is executed before the collection process is performed.

[Step S200]

At step S200, the self-diagnosis processor 136 may determine whether there is an output of a light signal. For example, the self-diagnosis processor 136 may cause the spectrum analyzer 120 to emit the light having the broadband spectrum, and may determine whether there is an output of the light signal from the spectrum analyzer 120 on the basis of the reception, by the light receiver of the spectrum analyzer 120, of the reflection light reflected by the gratings 118*b*. The process may proceed to step S202 if there is no output of the light signal (step S200: NO), in consideration of disconnection (or the breakage) in the fiber optic sensor 118. The process may proceed to step S206 if there is an output of the light signal (step S200: YES), in consideration of no disconnection in the fiber optic sensor 118.

[Step S202]

When there is no output of the light signal at step S200 (step S200: NO), at step S202, the self-diagnosis processor 136 may measure a response time. For example, the self-diagnosis processor 136 may cause an unillustrated spectrum analyzer, different from the spectrum analyzer 120 used for the collection process, to emit light, and may measure a time (i.e., the response time) until which the reflection light is received. Note that the self-diagnosis processor 136 may use another spectrum analyzer in one example illustrated in FIG. 3, however, the spectrum analyzer 120 itself or any other measuring instrument may be used to measure the response time, as long as a time taken from the emission of light to the reception of the reflection light is measurable.

It is to be noted that a light signal based on reflection light reflected from a breakage portion is still measurable, even if the disconnection occurs in the fiber optic sensor 118 and the output of the light signal based on the reflection light reflected from the gratings 118*b* is absent at step S200 accordingly. For example, the self-diagnosis processor 136 may identify a location at which the breakage occurs, on the basis of the principle of Optical Time Domain Reflectometer (OTDR) and on the basis of the time taken from the emission of light to reception of the light reflected from the breakage portion. Thus, the self-diagnosis processor 136 is able to identify whether the disconnection occurs in the sensor device, e.g., the gratings 118*b*, or whether the disconnection occurs in a cable part, e.g., the optical fiber.

[Step S204]

After measuring the response time at step S202, the self-diagnosis processor 136 may provide a notification on the breakage portion at step S204. In other words, the self-diagnosis processor 136 outputs an error. For example, the self-diagnosis processor 136 may cause the display 114 to display the identified breakage portion. The self-diagnosis process may end after performing step S204.

[Step S206]

When there is an output of the light signal at step S200 (step S200: YES), at step S206, the self-diagnosis processor 136 may perform a process related to calibration measurement. For example, the self-diagnosis processor 136 may cause the spectrum analyzer 120 to emit light having an intensity that is previously set for calibration purpose, and may cause the spectrum analyzer 120 to output a light signal based on the reflection light.

[Step S208]

After performing the calibration measurement at step S206, the self-diagnosis processor 136 may determine whether an output value of the calibration falls within a proper range. For example, the self-diagnosis processor 136 may obtain a temperature near the structure measured by an unillustrated thermometer. The self-diagnosis processor 136 may also calculate a stress that acts on the target TG of the structure, on the basis of a weight of the structure or a total weight of a loaded article mounted on the structure, both measured by an unillustrated weight sensor, for example.

Further, the self-diagnosis processor 136 may read table information related to the proper range stored in the storage 110. In an example implementation, the proper range of the calibration may be so set as to be associated with the stress and the temperature. The self-diagnosis processor 136 may identify, from the table information, the proper range that corresponds to the obtained temperature and to the calculated stress.

In this example way, the self-diagnosis processor 136 may determine whether the output value of the calibration falls within the proper range. The process may proceed to step S212 if the output value of the calibration falls within the proper range (step S208: YES), in consideration of no deterioration in the adhesive of the fiber optic sensor 118. The process may proceed to step S210 if the output value of the calibration falls outside the proper range (step S208: NO), in consideration of the deterioration in the adhesive of the fiber optic sensor 118.

[Step S210]

When the output value of the calibration falls outside the proper range at step S208 (step S208: NO), at step S210, the self-diagnosis processor 136 may provide a notification on the deterioration in the adhesive. In other words, the self-diagnosis processor 136 outputs an error. For example, the self-diagnosis processor 136 may cause the display 114 to display a notification notifying that the adhesive of the fiber optic sensor 118 is deteriorated. The self-diagnosis process may end after performing step S210.

[Step S212]

When the output value of the calibration falls within the proper range at step S208 (step S208: YES), at step S212, the vibration controller 130 may apply the vibration. For example, the vibration controller 130 may control the vibrator 116 to thereby vibrate or apply the vibration to the target TG.

[Step S214]

At step S214, the self-diagnosis processor 136 may determine whether there is a significant difference. For example, the self-diagnosis processor 136 may cause, during the application of the vibration, the spectrum analyzer 120 to emit the light having the broadband spectrum, and may cause the spectrum analyzer 120 to detect the wavelength of the reflection light. Thereafter, the self-diagnosis processor 136 may determine whether the wavelength of the reflection light shows a significant difference with respect to a previous measurement value. The process may proceed to step S216 if there is a significant difference (step S214: YES), in consideration of detachment of all or a part of the adhesive of the fiber optic sensor 118. The self-diagnosis process may end if there is no significant difference (step S214: NO), in consideration of no detachment of the adhesive of the fiber optic sensor 118.

[Step S216]

When there is a significant difference at step S214 (step S214: YES), at step S216, the self-diagnosis processor 136 may provide a notification on the detachment of the adhesive. In other words, the self-diagnosis processor 136 outputs an error. For example, the self-diagnosis processor 136 may cause the display 114 to display a notification notifying that the adhesive of the fiber optic sensor 118 is detached. The self-diagnosis process may end after performing step S216.

The health diagnosis processor 134 may perform the health diagnosis process, if none of the errors are outputted upon the execution of the foregoing example self-diagnosis process.

The diagnosis apparatus 100 according to the foregoing example implementation makes a diagnosis related to whether the fiber optic sensor 118 itself functions normally, on the basis of the above-described example self-diagnosis process. This eliminates the necessity of providing human resources for making the diagnosis, making it possible to achieve full automation from the self-diagnosis process to the collection process and to the health diagnosis process. For example, the diagnosis apparatus 100 makes it possible to perform the self-diagnosis process easily even in a situation where the fiber optic sensor 118 is positioned at a high altitude, or where examination is not performable unless any component of the structure is removed, making it possible to reduce a work burden.

Although some implementations of the technology have been described in the foregoing by way of example with reference to the accompanying drawings, the technology is by no means limited to the implementations described above.

For example, the fiber optic sensor 118 in the foregoing example implementation may utilize the fiber bragg grating. In an alternative example implementation, the fiber optic sensor 118 may utilize any other scheme. Further, in an alternative example implementation, the fiber optic sensor 118 may measure a physical quantity, a chemical quantity, or any other quantity of the target TG on the basis of a change in any other characteristic other than or in addition to the wavelength of the light. Non-limiting examples of such a characteristic may include an intensity, a phase, a frequency, and a polarization.

The diagnosis apparatus 100 according to the foregoing example implementation may include the health diagnosis processor 134. Providing the health diagnosis processor 134 helps to achieve the full automation from the self-diagnosis process to the collection process and to the health diagnosis process. The health diagnosis processor 134, however, is not necessarily an essential feature. In an alternative example implementation, the diagnosis apparatus 100 may not include the health diagnosis processor 134.

The diagnosis apparatus 100 according to the foregoing example implementation may include the vibrator 116. Providing the vibrator 116 helps to detect the damage in the health diagnosis process, and helps to detect the detachment of the adhesive in the self-diagnosis process. The vibrator 116, however, is not necessarily an essential feature. In an alternative example implementation, the diagnosis apparatus 100 may not include the vibrator 116.

The proper range in the foregoing example implementation may be associated with one or both of the stress and the temperature. The stress and the temperature are greatly influential to the output value of the calibration. Hence, setting the proper range such that the proper range is associated with one or both of the stress and the temperature helps to evaluate the fiber optic sensor 118 appropriately. The proper range may, however, be associated with any other physical quantity other than or in addition to the stress and/or the temperature.

According to any implementation of the technology, it is therefore possible to automate measurement that utilizes the fiber optic sensor.

The controller 122 illustrated in FIG. 1 is implementable by circuitry including at least one semiconductor integrated circuit such as at least one processor (e.g., a central processing unit (CPU)), at least one application specific integrated circuit (ASIC), and/or at least one field programmable gate array (FPGA). At least one processor is configurable, by reading instructions from at least one machine readable non-transitory tangible medium, to perform all or a part of functions of the controller 122. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and a SRAM, and the nonvolatile memory may include a ROM and a NVRAM. The ASIC is an integrated circuit (IC) customized to perform, and the FPGA is an integrated circuit designed to be configured after manufacturing in order to perform, all or a part of the functions of the controller 122 illustrated in FIG. 1.

It should be appreciated that modifications and alterations may be made by persons skilled in the art without departing from the scope as defined by the appended claims. The technology is intended to include such modifications and alterations in so far as they fall within the scope of the appended claims or the equivalents thereof.

The invention claimed is:

1. A diagnosis apparatus comprising:
    a fiber optic sensor configured to be disposed on a target being a part of a structure, the fiber optic sensor including:
        a core through which light passes, and
        a grating that has a refractive index different from a refractive index of any other part of the core and allows reflection light having a specific wavelength, out of light having a broadband spectrum, to be reflected from the grating;
    a vibrator configured to be disposed on the target and to vibrate the target; and
    a circuitry coupled to the fiber optic sensor and the vibrator;

wherein the circuitry is configured to cause a diagnosis process to be executed by:
calculating distortion measured when the target is vibrated by the vibrator and temperature calculated by using the reflection light,
detecting damage in a region from the vibrator to the fiber optic sensor by using the distortion, and
determining that the structure is not healthy when the damage is detected or when the temperature is in a predetermined range; and
wherein the circuitry is configured to cause a self-diagnosis process to be executed by at least one of:
detecting disconnection in the fiber optic sensor when there is no reflection light,
detecting deterioration in an adhesive of the fiber optic sensor on a basis of a stress that acts on the target of the structure, the stress calculated by using a temperature measured by a thermometer and a weight of the structure measured by a weight sensor, and
detecting detachment of an adhesive of the fiber optic sensor on a basis of comparison of a first wavelength of first reflection light with a second wavelength of second reflection light prior to the first reflection light.

2. The diagnosis apparatus according to claim 1, further comprising a health diagnosis processor configured to diagnose, on a basis of the measurement data collected by the collection processor, a health of a structure that is provided with the fiber optic sensor.

3. A diagnosis apparatus comprising:
a fiber optic sensor configured to be disposed on a target being a part of a structure, the fiber optic sensor including:
a core through which light passes, and
a grating that has a refractive index different from a refractive index of any other part of the core and allows reflection light having a specific wavelength, out of light having a broadband spectrum, to be reflected from the grating;
a vibrator configured to be disposed on the target and to vibrate the target; and
a circuitry coupled to the fiber optic sensor and the vibrator;
wherein the circuitry is configured to cause a diagnosis process to be executed by:
calculating distortion measured when the target is vibrated by the vibrator and temperature calculated by using the reflection light,
detecting damage in a region from the vibrator to the fiber optic sensor by using the distortion, and
determining that the structure is not healthy when the damage is detected or when the temperature is in a predetermined range; and
wherein the circuitry is configured to cause a self-diagnosis process to be executed by:
detecting deterioration in an adhesive of the fiber optic sensor on a basis of a stress that acts on the target of the structure, the stress calculated by using a temperature measured by a thermometer and a weight of the structure measured by a weight sensor, and
detecting detachment of an adhesive of the fiber optic sensor on a basis of comparison of a first wavelength of first reflection light with a second wavelength of second reflection light prior to the first reflection light.

4. A diagnosis apparatus comprising:
a fiber optic sensor configured to be disposed on a target being a part of a structure, the fiber optic sensor including:
a core through which light passes, and
a grating that has a refractive index different from a refractive index of any other part of the core and allows reflection light having a specific wavelength, out of light having a broadband spectrum, to be reflected from the grating;
a vibrator configured to be disposed on the target and to vibrate the target; and
a circuitry coupled to the fiber optic sensor and the vibrator;
wherein the circuitry is configured to cause a diagnosis process to be executed by:
calculating distortion measured when the target is vibrated by the vibrator and temperature calculated by using the reflection light,
detecting damage in a region from the vibrator to the fiber optic sensor by using the distortion, and
determining that the structure is not healthy when the damage is detected or when the temperature is in a predetermined range; and
wherein the circuitry is configured to cause a self-diagnosis process to be executed by:
detecting disconnection in the fiber optic sensor when there is no reflection light, and
detecting detachment of an adhesive of the fiber optic sensor on a basis of comparison of a first wavelength of first reflection light with a second wavelength of second reflection light prior to the first reflection light.

5. A diagnosis apparatus comprising:
a fiber optic sensor configured to be disposed on a target being a part of a structure, the fiber optic sensor including:
a core through which light passes, and
a grating that has a refractive index different from a refractive index of any other part of the core and allows reflection light having a specific wavelength, out of light having a broadband spectrum, to be reflected from the grating;
a vibrator configured to be disposed on the target and to vibrate the target; and
a circuitry coupled to the fiber optic sensor and the vibrator;
wherein the circuitry is configured to cause a diagnosis process to be executed by:
calculating distortion measured when the target is vibrated by the vibrator and temperature calculated by using the reflection light,
detecting damage in a region from the vibrator to the fiber optic sensor by using the distortion, and
determining that the structure is not healthy when the damage is detected or when the temperature is in a predetermined range; and
wherein the circuitry is configured to cause a self-diagnosis process to be executed by at least one of:
detecting disconnection in the fiber optic sensor when there is no reflection light, and
detecting deterioration in an adhesive of the fiber optic sensor on a basis of a stress that acts on the target of the structure, the stress calculated by using a temperature measured by a thermometer and a weight of the structure measured by a weight sensor.

* * * * *